United States Patent [19]

Miyoshi et al.

[11] 4,266,979
[45] May 12, 1981

[54] OXYGEN SENSOR CERAMIC AND PROCESS FOR PREPARING THE SAME

[75] Inventors: Tadahiko Miyoshi; Takeo Yamazaki, both of Hitachi, Japan

[73] Assignee: Hitachi, Ltd., Tokyo, Japan

[21] Appl. No.: 80,469

[22] Filed: Oct. 1, 1979

[30] Foreign Application Priority Data

Sep. 29, 1978 [JP] Japan ............................. 53/119312

[51] Int. Cl.³ ..................... C04B 35/48; C01N 27/58
[52] U.S. Cl. ................................................ 106/57
[58] Field of Search ............... 106/57; 204/195 S, 1 S

[56] References Cited

U.S. PATENT DOCUMENTS

| | | | |
|---|---|---|---|
| 3,334,962 | 8/1967 | Clearfield | 106/57 |
| 3,533,815 | 10/1970 | Baldwin | 106/57 |
| 3,620,781 | 11/1971 | Garvie | 106/57 |
| 4,183,798 | 1/1980 | Esper et al. | 106/57 |

OTHER PUBLICATIONS

Wheat, T. A., "Microstructure of Thermal-Shock Resistant Zirconia" Journal Canadian Ceramic Society, vol. 44, 1975 pp. 7-15.

Dueker, H., et al., "Ceramic Aspects of the Bosch Lambda-Sensor," Paper Delivered at Automotive Engineering Congress and Exposition, Detroit, Mich., Feb. 24-28, 1975, Society of Automotive Engineers.

Primary Examiner—O. R. Vertiz
Assistant Examiner—Mark Bell
Attorney, Agent, or Firm—Craig & Antonelli

[57] ABSTRACT

Oxygen sensor ceramic of solid electrolyte of zirconia-yttria system comprises aggregates of cubic zirconia grains having an average grain size of 2–10 μm and monoclinic zirconia grains having an average grain size of 0.2–1 μm, the appregates of the cubic zirconia grains being in contact with one another, and the monoclinic zirconia grains being distributed as aggregates in clearances among the aggregates of the cubic zirconia grains, and has a high thermal shock resistance, a high mechanical strength and a resistivity equal to that of the ceramic consisting only of cubic zirconia grains. The oxygen sensor ceramic is prepared by mixing zirconia powder having a grain size of 0.1–0.5 μm with 4–8% by mole of yttria powder having an average grain size of 0.5–5 μm, on the basis of total mixture, and molding and firing the mixture at 1,400°–1,550° C.

8 Claims, 4 Drawing Figures 1.0µ

1.0µ

OXYGEN SENSOR CERAMIC AND PROCESS FOR PREPARING THE SAME

This invention relates to an oxygen sensor ceramic, and particularly to an oxygen sensor ceramic of a solid electrolyte of a zirconia-yttria ($ZrO_2$—$Y_2O_3$) system and a process for preparing the oxygen sensor ceramic. The present oxygen sensor ceramic is used as an exhaust gas sensor for internal combustion engines of automobiles, etc., or combustion apparatus such as boiler, etc.

Recently, a system for detecting an oxygen concentration of exhaust gas to control a fuel supply system by feedback has been proposed as measures for controlling the exhaust gas from internal combustion engines on automobiles, etc. For reasons that an output can be changed stepwise for an air-fuel ratio of the air and the fuel to be supplied to an internal combustion engine, and the a stable output can be obtained in a wide temperature range from a low temperature to a high temperature (about 300°–900° C.), a solid electrolyte comprised of zirconia-yttria system has been generally utilized as the oxygen sensor ceramic.

When the oxygen sensor ceramic is used on automobiles, it is required that it can withstand a severe thermal shock such as 30°–50° C./sec, depending upon a running condition. Furthermore, it is required that it has a durability corresponding to more than 100,000 km running at a maximum speed (sensor temperature: about 900° C.). Furthermore, it is required that it has a mechanical strength that can withstand vibration test of about 60 G.

In the prior art oxygen sensor ceramic of zirconia-yttria system, a solid electrolyte comprised of cubic zirconia ceramic containing 7–10% by mole of yttria has been usually used (H. Dueker et al: Ceramic Aspect of the Bosch Lambda-Sensor, Papers 750223 presented at Automotive Engineering Congress and Exposition, Detroit, Mich., Feb. 24–28, 1975).

However, such ceramic has a large thermal expansion coefficient such as $100$–$120 \times 10^{-7}$/°C., and thus is not strong against a sudden thermal shock. Thus, the ceramic has such a drawback that it is readily cracked by a severe thermal shock of 30°–50° C./sec. required for automobiles.

To improve the thermal shock resistance of zirconia ceramic, a process for preparing a partially stabilized ceramic by adding a smaller amount of calcia (CaO), magnesia (MgO), or the like to zirconia than the necessary amount for stabilizing zirconia, sintering the ceramic at a high temperature, and sufficiently annealing the ceramic in a cooling step, thereby crystallizing out monoclinic zirconia at the boundary of cubic zirconia has been recently proposed (U.S. Pat. No. 3,620,781).

However, even if said process is applied to ceramics of zirconia-yttria system, it is difficult to obtain a ceramic having a good thermal shock resistance in a wide range of about 300° to about 900° C., and a new problem has been brought about in that an inside resistance of ceramics of such a zirconia-yttria system is increased owing to the influence of monoclinic zirconia having a higher resistance than cubic zirconia, and the sensor cannot be used sufficiently even down to the low temperature.

An object of the present invention is to provide an oxygen sensor ceramic of zirconia-yttria system having a low inside resistance in a wide temperature range, a good thermal shock resistance, and a high mechanical strength.

Another object of the present invention is to provide a process for preparing such an oxygen sensor ceramic.

The oxygen sensor ceramic according to the present invention comprises a solid electrolyte of zirconia-yttria system, comprising aggregates of cubic zirconia grains having an average grain size of 2–10 μm and monoclinic zirconia grains having an average grain size of 0.2–1 μm, the aggregates of the cubic zirconia grains being in contact with one another, and the monoclinic zirconia grains being distributed as aggregates in clearances among the aggregates of the cubic zirconia grains.

The process for preparing an oxygen sensor ceramic of zirconia-yttria system according to the present invention comprises mixing 4 to 8% by mole of yttria powder having an average grain size of 0.5–5 μm with zirconia powder having an average grain size of 0.1–0.5 μm on the basis of total mixture, molding the resulting mixture and firing the mixture at a temperature in a range of 1,400° to 1,550° C.

As a result of various studies, the present inventors have found that the thermal shock resistance and electrical resistance of ceramics of zirconia-yttria system are in a close relation to an inside structure of the ceramics. That is, in order to decrease an electrical resistance of ceramics, aggregates of cubic zirconia grains having a relatively low electrical resistance must be present in contact with one another in sintered ceramics. Since an electric current (i.e. oxygen ions) passes mainly through the aggregates of cubic zirconia grains in said structure, no considerably large influence is given to the electrical resistance of ceramics on the whole, even if monoclinic zirconia grains having a relatively large electrical resistance are present in the sintered ceramics at the same time.

In order to improve a thermal shock resistance of ceramics, fine monoclinic zirconia grains must be present as aggregates in clearances among the aggregates of cubic zirconia grains. Since a compressive stress based on a volumetric expansion due to a phase transition of from a cubic system to a monoclinic system in a cooling step after the firing of the ceramics is due to the aggregates of monoclinic zirconia grains, cracks are barely propagated; and in the case of a large thermal shock, a large number of microcracks are produced in the aggregates of monoclinic zirconia grains, and act as an absorber of thermal shock energy. That is, the propagation of cracks in ceramics can be prevented thereby, and consequently the heat shock resistance of ceramics can be improved.

It is desirable that the monoclinic zirconia grains have an average grain size of about 0.2 to about 1 μm. If the grain size exceeds about 1 μm, the size of microcracks produced in the aggregates of monoclinic zirconia grains is increased correspondingly, and consequently the thermal shock resitance of ceramics is lowered. As a result of studies, the present inventors have found that, when the monoclinic zirconia grains have an average grain size of not more than about 1 μm, a ceramic capable of withstanding a thermal shock of 30°–50° C./sec can be obtained. When the grain size is less than about 0.2 μm, a contact area among the individual grains in the aggregates of the monoclinic zirconia grains is reduced, and consequently the bonding among the monoclinic zirconia grains is locally broken by the influence of phase transition of from the cubic system to the monoclinic system in the cooling step after the firing of ceramics, and a portion of the monoclinic zirconia grains is peeled off, lowering the mechanical strength of the ceramics and lowering the thermal shock resistance.

It is important for increasing the thermal shock resistance of ceramics that the monoclinic zirconia grains are present as aggregates in clearances among the aggregates of cubic zirconia grains. Since the cubic zirconia generally has a larger thermal expansion coefficient than the monoclinic zirconia, cracks are produced mainly among the cubic zirconia grains when a thermal shock is applied to the ceramics, and the cracks propagate through the ceramics, and a breakage proceeds in this manner.

According to the ceramic structure of the present invention, an energy of cracks produced among the cubic zirconia grains is absorbed in the aggregates of the monoclinic zirconia grains present in the clearances among the aggregates of cubic zirconia grains, and thus a thermal shock resistance is increased. When the number of monoclinic zirconia grains constituting the aggregates is small, the energy of cracks cannot be thoroughly absorbed, and cracks pass through the aggregates of monoclinic zirconia grains, propagating the cracks throughout the ceramic. To withstand the thermal shock of 30°–50° C./sec required for an automobile exhaust gas sensor, more than about 100 monoclinic zirconia grains are necessary for one aggregate. To satisfy this condition, it has been found that the average grain size of cubic zirconia grains is at least about 5 times the average grain size of monoclinic zirconia grains.

The present zirconia oxygen sensor ceramic contains aggregates of monoclinic zirconia grains in the ceramic, and thus repeated use in the temperature range where the phase transition of from the monoclinic system to the cubic system or vice versa takes place is not preferable. When the phase transition is repeted, the bonding among the monoclinic zirconia grains is broken, and the mechanical strength of the ceramics is liable to be lowered. Therefore, it is desirable to lower an yttria concentration of the monoclinic zirconia and keep a phase transition temperature of from the monoclinic system to the cubic system or vice versa higher. To withstand the use at a maximum 900° C. required for the automobile exhaust gas sensor, it is desirable that an average yttria concentration in the monoclinic zirconia is not more than about 1% by mole.

Sintering temperature of zirconia is as high as 1,800° C. in the case of a single zirconia, and admixture of said amount of yttria can make the sintering readily proceed and can also lower the sintering temperature. Therefore, when no yttria is contained in the monoclinic zirconia, the sinterability of the aggregates of monoclinic zirconia grains becomes poor, and the bonding among the monoclinic zirconia grains becomes weak. Aggregates of monoclinic zirconia grains are peeled off by the influence of phase transition of from the cubic system to the monoclinic system in the cooling step after the firing of ceramics, considerably lowering the mechanical strength of ceramics. An amount of yttria for increasing the sinterability of zirconia must be at least about 0.01% by mole on the basis of total mixture, and an average concentration of yttria in the monoclinic zirconia must be at least 0.01% by mole.

It is desirable that the cubic zirconia grains have an average grain size of 2–10 $\mu$m. When the average grain size is too large, a larger stress is produced in the cubic zirconia grains when a thermal shock is given to the ceramic, and the length of cracks produced is made larger thereby. That is, the energy of cracks cannot be thoroughly absorbed by the aggregates of monoclinic zirconia grains and the mechanical strength of the ceramics is lowered, even if the energy is absorbed. To withstand the thermal shock of 30°–50° C./sec, it is necessary that the average grain size of cubic zirconia grains is not more than 10 $\mu$m. When the average grain size of cubic zirconia grains is too small, the resistance of ceramic is increased by the influence of resistance when an electric current passes through the grain boundary. Thus, it is desirable that the average grain size of cubic zirconia grains is at least about 2 $\mu$m.

It is desirable that an average concentration of yttria in the cubic zirconia is in a range of 7–10% by mole, and ceramics of particularly low resistance can be prepared in said range.

The amount of monoclinic zirconia in the zirconia ceramic constituting the present oxygen sensor ceramic is desirably in a range of 10–50% by mole on the basis of total mixture. When the amount of monoclinic zirconia is smaller, the number of aggregates of monoclinic zirconia grains present in the clearances among the aggregates of cubic zirconia grains is decreased, lowering the thermal shock resistance of the ceramic. To attain the thermal shock resistance of 30°–50° C./sec or higher, the amount of monoclinic zirconia of at least 10% by mole must be present in the ceramic. When the amount of monoclinic zirconia exceeds 50% by mole on the other hand, the number of aggregates of monoclinic zirconia grains is too much increased, and the aggregates of cubic zirconia grains will not be brought into contact with one another. That is, the resistance of the ceramic is considerably increased by the influence of monoclinic zirconia having a relatively high resistance.

The present oxygen sensor ceramic of zirconia-yttria system can be readily prepared by uniformly mixing zirconia powder of monoclinic system having an average grain size of about 0.1 to about 0.5 $\mu$m with about 4 to about 8% by mole of yttria powder having an average grain size of about 0.5 to about 5 $\mu$m on the basis of total mixture, admixing the resulting mixture with a binder such as polyvinyl alcohol or paraffin, molding the mixture, and then firing the molded mixture as a temperature of about 1,400° to about 1,500° C. for about 1 to about 3 hours. In addition to yttria, a small amount of an additive such as alumina ($Al_2O_3$), silica ($SiO_2$), etc. can be added thereto to lower the sintering temperature when fired. After the mixing of zirconia powder with yttria powder, the resulting mixture can be calcined at a temperature of about 1,100° to about 1,300° C., and pulverized to a grain size of about 0.5 $\mu$m, and the resulting powder can be molded and fired in the same manner as above.

According to the present process, zirconia and yttria are mutually diffused when fired, and the portion containing a larger amount of diffused yttria turns into cubic zirconia, and the portion containing a smaller amount of diffused yttria remains as the monoclinic zirconia. The fastest growth of zirconia grains takes place when about 7 to about 12% by mole of yttria is contained therein, whereas zirconia grains having a smaller yttria content grows slowly. Thus, the average grain size of cubic zirconia grains can be brought into a range of 2–10 $\mu$m and at the same time the average grain size of monoclinic zirconia grains can be brought into a range of 0.2–1 $\mu$m. Furthermore, yttria is radially diffused into zirconia from the admixed yttria grains, and thus almost spherical aggregates of cubic zirconia taking yttria as their centers can be brought into contact with one another by properly selecting the average distance between yttria grains in the mixture and firing conditions. Zirconia other than said spherical aggregates of cubic zirconia grains remains as the monoclinic zirconia and takes such a structure that there are aggregates of monoclinic zirconia grains just in the clearance among the spherical aggregates of cubic zirconia grains.

The present invention will be described in detail below, referring to the accompanying drawings.

Figure 1:
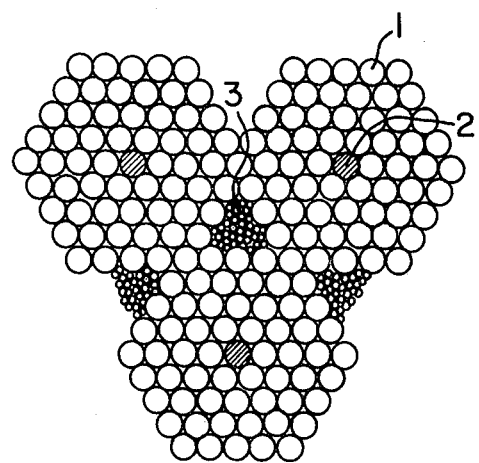
FIG. 1 is a schematic view showing a structure of the present oxygen sensor ceramic of zirconia-yttria system.

In FIG. 1, numeral 1 is a cubic zirconia grain, 2 is a position at which yttria grains originally existed, 3 is an aggregate of monoclinic zirconia grains. The present oxygen sensor ceramic of zirconia-yttria system as schematically shown in FIG. 1 is obtained in said manner according to the present process.

Firing temperature must be in a range of about 1,400° to about 1,550° C. If the firing temperature exceeds 1,550° C., both cubic zirconia grains and monoclinic zirconia grains grow beyond the grain size range of the present invention, lowering the thermal shock resistance of ceramics. At the same time, yttria diffuses into the monoclinic zirconia, whereby the average yttria concentration of the monoclinic zirconia exceeds about 1% by mole, and the phase transition temperature of from the monoclinic system to the cubic system, or vice versa is made lower than 900° C. This is a great disadvantage. If the firing temperature exceeds 1,550° C., and the amount of admixed yttria is as large as 7-8% by mole or the grain size of yttria powder is as small as about 0.5 to about 1 μm, the number of aggregates of monoclinic zirconia grains is decreased, or the number of monoclinic zirconia grains constituting the individual aggregates is decreased, whereby the thermal shock resistance of ceramics is lowered. If the firing temperature is lower than 1,400° C. on the other hand, the sinterability of the ceramics is made poor, and also the mechanical strength of the ceramics is lowered. Furthermore, the diffusion distance of yttria powder is shortened, and the almost spherical aggregates of cubic zirconia taking yttria as their centers are not brought into contact with one another, and the electrical resistance of ceramics is increased by the influence of the aggregates of monoclinic zirconia grains. These are advantages.

It is desirable that the grain size of zirconia powder to be used as the raw material is in a range of about 0.1 to about 0.5 μm. If the grain size exceeds 0.5 μm, the sinterability of the powder is lowered, and the sintering of ceramics at the low temperature of 1,400° to 1,550° C. is not sufficient, and the mechanical strength is lowered. If the grain size of zirconia powder is less than 0.1 μm, a hygroscopic property is given to the powder, or the powder is more scatterable, and the handling of the raw material and molding of ceramics become difficult, readily causing a lamination.

It is desirable to use yttria powder having a grain size of about 0.5 to about 5 μm as the raw material. If yttria having a grain size of more than about 5 μm is used, it must be mixed with zirconia in a ball mill, etc. to pulverize the yttria, or it must be once mixed with zirconia, calcined, and then pulverized to a grain size of about 0.5 to about 1 μm. If the grain size of yttria exceeds 5 μm, the yttria concentration in the zirconia near the yttria grains becomes too high, and the sinterability becomes worse in those regions, lowering the mechanical strength of ceramics. If the grain size of yttria powder is too smaller, the number of yttria grains to be distributed in the zirconia is increased, and yttria is widely distributed in the zirconia, decreasing the number of aggregates of monoclinic zirconia grains or the number of monoclinic zirconia grains constituting the individual aggregates, consequently the thermal shock resistance of ceramics is lowered.

If the amount of yttria to be added exceeds 8% by mole, the number of aggregates of monoclinic zirconia grain is decreased or the number of monoclinic zirconia grains constituting the individual aggregates is decreased for the same reasons as above, and consequently the thermal shock resistance of the ceramics is lowered. If the amount of yttria to be added is less than 4% by mole, the number of yttria grains to be distributed in the zirconia is decreased, and the region where yttria is diffused in the zirconia is so reduced that the almost spherical aggregates of cubic zirconia grains taking the yttria as their centers will not be brought into contact with one another, and the electrical resistance of the ceramics is disadvantageously increased. Thus, it is desirable that the amount of yttria to be added is within a range of 4-8% by mole.

In the foregoing, description has been made of a binary system of zirconia-yttria, but the effects of the present invention will not be changed, even if such additives as alumina ($Al_2O_3$), silica ($SiO_2$), iron oxide ($Fe_2O_3$), calcia (CaO), magnesia (MgO), etc. are added thereto. Compounds capable of being changed into their oxides by heating, for example, carbonates, oxalates, nitrates, organometallic salts, etc. can be used as the raw materials in place of zirconia, yttria, etc. In the case of these compounds, the grain size of the oxides just formed by heating has a great influence upon the sinterability of ceramics.

The present invention will be described in detail, referring to Examples.

EXAMPLE 1

Figure 2:
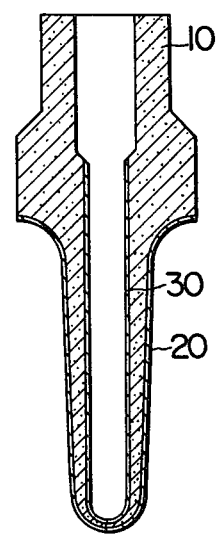
FIG. 2 is a view showing a structure of a sensor prepared according to one embodiment of the present invention.

Zirconium oxide (purity: 99.9%, average grain size: 0.2 μm, made by Kojundo Kagaku Kenkyusho, Ltd, Japan) was admixed with 10.47% by weight (6% by mole) of yttrium oxide (purity: 99.9%, average grain size: 8 μm, made by Dai-ichi Kigenso Kagaku Kogyo K.K., Ltd, Japan and 0.1% by weight of silicon dioxide "Bitaseal #1500" (a trademark of a product made by Tagi Kagaku K.K., Ltd, Japan) on the basis of total mixture and mixed by a mortar and pestle for 2 hours. Then, the resulting mixture was calcined in an electric oven at 1,200° C. for two hours, and then pulverized to an average grain size of 0.5 μm in a vibration mill made of $Al_2O_3$ over a period of 10 hours. After admixed with 3% by weight of paraffin as a binder, the resulting powder was molded into a tube with one closed end, and fired in the air at 1,500° C. for one hour to form a sensor element. Then, a chloroplatinic acid solution was applied to both inside and outside of the sensor element in a tube form with one closed end, and then the sensor element was baked at 800° C. for 10 minutes to form platinum electrodes on both sides. The structure of the resulting sensor element is shown in FIG. 2, where numeral 10 is a ceramic of zirconia-yttria system, and 20 and 30 are platinum electrodes.

Figure 3:
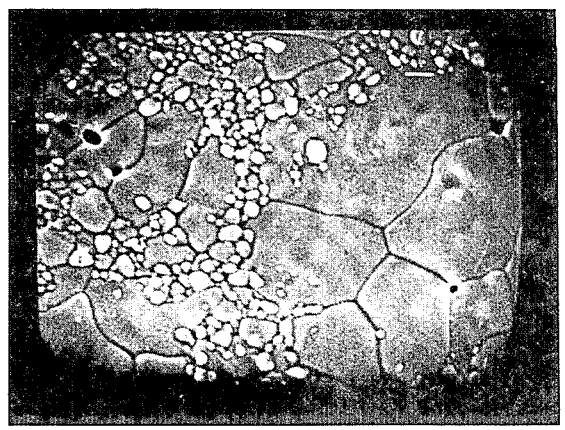
FIGS. 3 and 4 are pictures of natural surface and fracture surface, respectively, of the oxygen sensor ceramic prepared according to one embodiment of the present invention, taken by a scanning type electron microscope.
Figure 4:
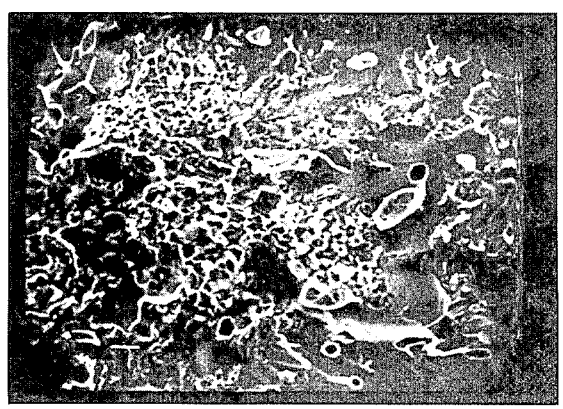

Natural surface and fracture surface of the resulting ceramic are shown in pictures of FIGS. 3 and 4, respectively, taken by a scanning type electron microscope.

It was found by investigation of yttria concentration distribution by an X-ray microanalyzer that the yttria concentration in the grains having a larger grain size (more than 1 μm) was about 7% by mole, whereas the yttria concentration in the grains having a smaller grain size (not more than 1 μm) was about 0.5% by mole. In view of the phase diagram that zirconia having an yttria concentration of more than about 6% by mole results in a cubic system at room temperature, whereas zirconia having an yttria concentration of less than about 2% by mole results in a monoclinic system, it is seen from FIGS. 3 and 4 that the ceramic obtained according to the present Example has such a structure that there are aggregates of monoclinic zirconia grains (yttria concentration: 0.5% by mole) having an average grain size of about 0.5 μm in the clearances among the aggregates of cubic zirconia grains (yttria concentration: 7% by mole) having an average grain size of about 5 μm.

It was also found by pulverizing the resulting ceramic and analyzing the resulting powder by an intensity of powder X-ray diffraction according to the following equation (1) that the amount of monoclinic zirconia in the ceramic was about 18% by mole.

$$= \frac{\text{Intensity of monoclinic system (111)} + \text{Intensity of monoclinic system (11}\bar{1}\text{)}}{\text{Intensity of cubic system (111)} + \text{Intensity of monoclinic system (111)} + \text{Intensity of monoclinic system (11}\bar{1}\text{)}}$$

It was also found by investigation using a high temperature X-ray camera that the phase transition temperature of from monoclinic system to cubic system of zirconia (which was deemed to be a temperature at which the amount of monoclinic zirconia was reduced to one-half of that at room temperature) was about 950° C.

Furthermore, the thermal expansion coefficient of the resulting ceramic was about $85 \times 10^{-7}/°C$. in a range of room temperature to 800° C.

The ceramic obtained according to the present Example had a large thermal shock resistance in a wide temperature range for the reasons that there are the aggregates of monoclinic zirconia grains in the clearances among the aggregates of cubic zirconia grains; the grain sizes of the cubic zirconia grains and monoclinic zirconia grains are in an appropriate range; and the phase transition temperature of from the monoclinic system to the cubic system is high. That is, even if ten repetitions of a test cycle of contacting the sensor element having one closed end as shown in FIG. 2, with a gas flame at a flame temperature of 1,050° C. for 30 seconds, and then exposing the element to air at room temperature for 2 minutes (which corresponds to a thermal shock of room temperature $\rightleftarrows$ 900° C. and 40° C./sec) were conducted, no crack was observed at all on the sensor element.

On the other hand, in the case of the sensor element consisting only of cubic zirconia ceramic or the sensor element comprising a partially stabilized ceramic fired at a high temperature, so far used in the relevant field, cracks appeared on the ceramics after one or two runs of said test cycle.

Even when the sensor element prepared according to the present Example was heated to 500° C., and dipped into water at 20° C., no cracks were observed at all on the ceramic.

In the present ceramic, aggregates of cubic zirconia grains of low electrical resistance were brought in contact with one another, as shown in FIGS. 3 and 4, and the electric current passed through these aggregates, and thus the resistivity of the ceramic was relatively low. That is, the resistivity at 300° C. (using an alternating current bridge at 1 kHz) was 200 kΩ·cm, which was almost equal to that of the prior art sensor element consisting only of cubic zirconia.

The present sensor element had a large mechanical strength, and even when it was mounted on an exhaust gas line of automobile engine, and subjected to a running test of 100,00 km, it had not problem.

EXAMPLE 2

Zirconium oxide (purity: 99.9%, average grain size: 0.1 μm, made by Kojundo Kagaku Kenkyusho, Ltd, Japan) was admixed with varied amounts of yttrium oxide (purity: 99.9%, average grain size: 3 μm; made by Dai-ichi Kigenso Kagaku Kogyo K.K., Ltd, Japan) and stirred in a vibration mill for 10 hours. Then, the resulting mixture was admixed with an aqueous polyvinyl alcohol solution, and molded into tubes with one closed end according to a rubber press method, and fired in the air.

Characteristics of the resulting ceramics obtained in varied amounts of yttrium oxide under varied firing conditions are given in Table 1.

TABLE 1

| Ceramic No. | Yttria added (mol %) | Firing temp. (°C.) | Firing time (h) | Monoclinic zirconia ||| Cubic zirconia ||| Cracks when thermal shock is given | Cracks when vibration test was conducted |
|---|---|---|---|---|---|---|---|---|---|---|---|
| | | | | Average grain size (μm) | Yttria concentration (mol %) | Amount (mol %) | Average grain size (μm) | Yttria concentration (mol %) | Resistivity at 300° C. (Ω·cm) | | |
| 1 | 2 | 1400 | 2 | 0.1 | <0.1 | 90 | 1 | 16 | 10M | — | — |
| 2 | " | 1500 | 1 | 0.4 | 0.2 | 75 | 3 | 8 | 5M | — | — |
| 3 | " | 1600 | 1 | 2 | 1.2 | 60 | 5 | — | — | appeared | none |
| 4 | 4 | 1300 | 1 | 0.1 | <0.01 | 73 | 0.5 | 14 | 2.5M | none | appeared |
| 5 | " | 1400 | 1 | 0.2 | 0.01 | 48 | 2 | 8 | 800K | none | none |
| 6 | " | 1400 | 3 | 0.3 | 0.1 | 38 | 5 | 7 | 600K | none | none |
| 7 | " | 1500 | 1 | 0.5 | 0.3 | 30 | 5 | 6 | 600K | none | none |
| 8 | " | 1550 | 1 | 1 | 0.8 | 25 | 8 | 6 | 500K | none | none |
| 9 | " | 1800 | 1 | 5 | 2 | 20 | 15 | — | — | appeared | none |
| 10 | 6 | 1300 | 1 | 0.1 | <0.01 | 56 | 0.5 | 14 | 1.5M | none | appeared |

TABLE 1-continued

| | | | | Monoclinic zirconia | | | Cubic zirconia | | | | Cracks when vibration test was conducted |
|---|---|---|---|---|---|---|---|---|---|---|---|
| Ceramic No. | Yttria added (mol %) | Firing temp. (°C.) | Firing time (h) | Average grain size (μm) | Yttria concentration (mol %) | Amount (mol %) | Average grain size (μm) | Yttria concentration (mol %) | Resistivity at 300° C. (Ω·cm) | Cracks when thermal shock is given | |
| 11 | " | 1400 | 2 | 0.2 | 0.1 | 35 | 2 | 10 | 300K | none | none |
| 12 | 6 | 1500 | 1 | 0.5 | 0.3 | 20 | 5 | 7 | 200K | none | none |
| 13 | " | 1550 | 1 | 1 | 1 | 12 | 10 | 7 | 150K | none | none |
| 14 | " | 1600 | 1 | 2 | 2 | 5 | 15 | 6 | — | appeared | none |
| 15 | " | 1800 | 1 | — | — | — | 20 | 6 | 100K | appeared | none |
| 16 | 8 | 1300 | 1 | 0.1 | <0.01 | 42 | 1 | 14 | 800K | none | appeared |
| 17 | " | 1400 | 1 | 0.2 | 0.1 | 20 | 2 | 10 | 200K | none | none |
| 18 | " | 1400 | 3 | 0.3 | 0.3 | 12 | 3 | 9 | 100K | none | none |
| 19 | " | 1500 | 1 | 0.5 | 0.5 | 10 | 5 | 9 | 80K | none | none |
| 20 | " | 1550 | 1 | 1 | 1 | 5 | 10 | 8 | — | appeared | none |
| 21 | " | 1600 | 1 | — | — | — | 8 | 8 | 70K | appeared | none |
| 22 | 10 | 1400 | 2 | 0.2 | <0.1 | 5 | 3 | 10 | — | appeared | appeared |
| 23 | " | 1500 | 1 | — | — | — | 7 | 10 | 150K | appeared | none |
| 24 | " | 1600 | 1 | — | — | — | 20 | 10 | 100K | appeared | none |

The thermal shock test results in Table 1 for the resulting ceramics were obtained by conducting 10 repetitions of a cycle of contacting with a gas flame at 1,050° C. for 30 seconds and then exposing to air at room temperature for 2 minutes, and the vibration test result was obtained by conducting a vibration test under 60 G for 30 seconds.

Ceramics Nos. 5, 6, 7, 8, 11, 12, 13, 17, 18, and 19 in Table 1 fall under the range of the present invention and had a good thermal shock resistance, a high mechanical strength, and a relatively low resistivity at 300° C. such as 80–800 kΩ·cm. Particularly, ceramics Nos. 11, 12, 13, 17, 18 and 19 having an yttria concentration of 7–10% by mole in the cubic zirconia and 10–35% by mole of monoclinic zirconia had a lower resistivity such as 80–300 kΩ·cm. The oxygen sensor ceramic of zirconia-yttria system having such a low resistivity can undergo a low temperature actuation because the inside electrical resistance of the sensor ceramic is low, and a feedback control can be advantageously made by the present ceramic at an idling of automobile or even at the start-up at a low exhaust gas temperature, which is a particular problem in the exhaust gas handling.

On the other hand, ceramics Nos. 1, 2, 4 and 10 had a larger amount of monoclinic zirconia grains, and the aggregates of cubic zirconia grains take an isolated structure in the monoclinic zirconia grains in the ceramics, and thus these ceramics had a high resistivity.

Ceramics Nos. 4, 10 and 16 had a low yttria concentration in the monoclinic zirconia, and thus had a poor sinterability of ceramics. Cracks appeared on the ceramics when subjected to the vibration test.

Ceramics Nos. 3, 9, 14, 15, 20, 21, 22, 23 and 24 had a low thermal shock resistance and cracks appeared when subjected to the thermal shock test for the reasons that the yttria concentration in the monoclinic zirconia is too high (Nos. 3, 9 and 14), the grain size of the monoclinic zirconia grains is too large (Nos. 3, 9 and 14), the amount of the monoclinic zirconia grains is too small (Nos. 14, 15, 20, 21, 22, 23 and 24), and the grain size of the cubic zirconia is too large (Nos. 9, 14, 15 and 24).

EXAMPLE 3

Zirconium oxide and yttrium oxide were mixed by a mortar and pestle for two hours, molded and fired while varying grain sizes of the raw materials. The results are shown in Table 2.

TABLE 2

| Ceramic No. | Grain size of zirconia (μm) | Yttria Grain size (μm) | Yttria Amount added (mol %) | Firing condition Temp. (°C.) | Firing condition Time (h) | Amount of monoclinic zirconia in ceramic (mol %) | Cracks when thermal shock is given | Cracks when subjected to vibration test |
|---|---|---|---|---|---|---|---|---|
| 25 | 0.1 | 0.5 | 6 | 1400 | 1 | 20 | none | none |
| 26 | " | 0.5 | " | 1500 | 1 | 12 | none | none |
| 27 | " | 5 | " | 1400 | 1 | 45 | none | none |
| 28 | " | 5 | " | 1500 | 1 | 30 | none | none |
| 29 | " | 8 | " | 1500 | 1 | 55 | — | appeared |
| 30 | 0.2 | 0.2 | " | 1400 | 1 | 8 | appeared | — |
| 31 | " | 0.2 | " | 1500 | 1 | 5 | appeared | none |
| 32 | " | 0.5 | " | 1500 | 1 | 10 | none | none |
| 33 | " | 3 | " | 1500 | 1 | 18 | none | none |
| 34 | 0.5 | 0.2 | " | 1500 | 1 | 5 | appeared | none |
| 35 | " | 3 | " | 1500 | 1 | 20 | none | none |
| 36 | " | 5 | " | 1500 | 1 | 30 | none | none |
| 37 | 0.5 | 8 | 6 | 1500 | 1 | 55 | — | appeared |
| 38 | 1.0 | 3 | " | 1500 | 1 | 20 | — | appeared |
| 39 | " | 3 | " | 1550 | 1 | 12 | — | appeared |
| 40 | " | 3 | " | 1600 | 1 | 5 | appeared | none |

In Table 2, ceramics Nos. 25, 26, 27, 28, 32, 33, 35 and 36 are within the range of the present invention, and had a good thermal shock resistance and a good mechanical strength.

On the other hand, ceramics Nos. 29 and 37 had a larger grain size of yttria grains, and ceramics Nos. 38 and 39 had a too large grain size of zirconia grains, and thus had a poor sinterability of ceramics and a problem in mechanical strength.

Ceramics Nos. 30, 31, 34 and 40 had a too small amount of monoclinic zirconia grains in the ceramics, and had a poor thermal shock resistance of the ceramics.

As described above, the present oxygen sensor ceramic had a high thermal shock resistance, a high mechanical strength, and a resistivity equal to that of the prior art oxygen sensor ceramic consisting only of cubic zirconia grains.

What is claimed is:

1. An oxygen sensor ceramic of a solid electolyte of a zirconia-yttria system, which comprises aggregates of cubic zirconia grains having an average grain size of 2–10 μm and monoclinic zirconia grains having an average grain size of 0.2–1 μm, the aggregates of said cubic zirconia grains being in contact with one another, and said monoclinic zirconia grains being distributed as aggregates in clearances among the aggregates of the cubic zirconia grains.

2. An oxygen sensor ceramic according to claim 1, wherein the cubic zirconia grains have an average grain size at least 5 times as large as that of the monoclinic zirconia grains.

3. An oxygen sensor ceramic according to claim 1 or 2, wherein an average yttria concentration in the monoclinic zirconia is in a range of 0.01–1% by mole.

4. An oxygen sensor ceramic according to claim 1 or 2, wherein an average yttria concentration in the cubic zirconia is in a range of 7–10% by mole.

5. An oxygen sensor ceramic according to claim 1 or 2, wherein an amount of the monoclinic zirconia in the ceramic is 10–50% by mole on the basis of total mixture.

6. A process for preparing an oxygen sensor ceramic, which comprises mixing monoclinic zirconia powder having a grain size of 0.1–0.5 μm with 4–8% by mole of yttria powder on the basis of the total mixture, said yttria powder having an average grain size of 0.5–5 μm, molding and firing the mixture at a temperature of 1,400°–1,550° C.

7. A process for preparing an oxygen sensor ceramic as set forth in claim 6, wherein the mixture of zirconia powder and yttrium powder is calcinated at a temperature of about 1100° to about 1300° C., and then pulverized to grain size of about 0.5 μm prior to molding.

8. A process for preparing an oxygen sensor ceramic as set forth in claim 6 or 7, wherein the mixture of zirconia powder and yttrium powder is mixed with a binder prior to molding.

* * * * *